United States Patent

Yoshida et al.

[11] Patent Number: 6,162,944
[45] Date of Patent: Dec. 19, 2000

[54] PROCESS FOR PRODUCTION OF N-CYCLOPROPYLANILINES AND INTERMEDIATES THEREFOR

[75] Inventors: Yasuo Yoshida; Kazuto Umezu; Yusuke Hamada; Fumiya Tabuchi, all of Shizuoka-ken, Japan

[73] Assignee: Ihara Chemical Industry Co., Ltd., Tokyo, Japan

[21] Appl. No.: 09/423,339

[22] PCT Filed: Mar. 27, 1998

[86] PCT No.: PCT/JP98/01395

§ 371 Date: Nov. 22, 1999

§ 102(e) Date: Nov. 22, 1999

[87] PCT Pub. No.: WO99/50226

PCT Pub. Date: Oct. 7, 1999

[51] Int. Cl.[7] .................................................. C07C 229/00
[52] U.S. Cl. .............................. 560/44; 564/405; 564/399
[58] Field of Search ............................. 560/44; 564/405, 564/399

[56] References Cited

FOREIGN PATENT DOCUMENTS

| 0 376 870 A1 | 7/1990 | European Pat. Off. . |
| 61-180728 | 8/1986 | Japan . |
| 10-87584 | 4/1998 | Japan . |

*Primary Examiner*—Samuel Barts
*Attorney, Agent, or Firm*—Kubovcik & Kubovcik

[57] ABSTRACT

Process for production of, from inexpensive raw materials of high commercial availability, N-cyclopropylanilines which are an important intermediate in producing a quinolonecarboxylic acid having a cyclopropyl group at the 1-position, a fluorine atom at the 6-position, and an alkyl group, an alkoxy group or a fluorine-substituted methoxy group at the 8-position (this quinolonecarboxylic acid is a useful synthetic antibacterial agent); and intermediates therefor. For example, a process for producing an N-cyclopropyl-3,4-difluoroaniline represented by the formula (4):

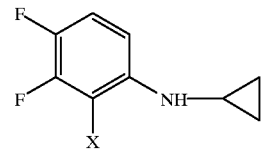

(4)

includes reacting, in the presence of an acid in an alcohol type solvent, a 3,4-difluoro-2-substituted-aniline with a 1-alkoxy-1-trialkylsilyloxycyclopropane to produce an N-alkoxycyclopropylaniline represented by the general formula (3):

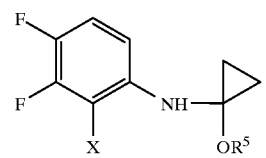

(3)

and then reducing the N-alkoxycyclopropylaniline.

5 Claims, No Drawings

PROCESS FOR PRODUCTION OF N-CYCLOPROPYLANILINES AND INTERMEDIATES THEREFOR

This application is a 371 of PCT/JP98/01395 filed Mar. 27, 1998.

TECHNICAL FIELD

The present invention relates to processes for production of N-cyclopropylanilines useful in production of a quinolonecarboxylic acid type synthetic antibacterial agent, as well as to intermediates therefor.

BACKGROUND ART

Quinolonecarboxylic acids, particularly, those having a cyclopropyl group at the 1-position, a fluorine atom at the 6-position and an alkyl group (see JP-A-62-215572 and JP-A-63-264461), an alkoxy group (see JP-A-63-198664 and JP-A-62-252772) or a fluorine-substituted methoxy group (JP-A-5-255183) at the 8-position are known to have an excellent antibacterial activity.

For production of such a quinolonecarboxylic acid, there have heretofore been proposed various processes. However, it is not known yet to produce a quinolonecarboxylic acid having a cyclopropyl group at the 1-position, a fluorine atom at the 6-position and an alkyl group, an alkoxy group or a fluorine-substituted methoxy group at the 8-position, via an N-cyclopropyl-2-substituted-3,4-difluoroaniline or an anilinomethylenemalonic acid derived therefrom.

For production of an aniline wherein a cyclopropyl group is bonded to the nitrogen atom, there is a report on a process which comprises reacting 1-ethoxy-1-trimethylsiloxycyclopropane with aniline in the presence of sodium cyanoborohydride [Tetrahedron Letters, Vol. 36, 7399 (1995)]. In this process, however, an N,N-dicyclopropyl group-containing product is generated in a large amount as a by-product, resulting in a low yield of the intended N-cyclopropyl group-containing product.

There are also reports on a process which comprises reacting 1-ethoxy-1-trimethylsilyloxycyclopropane with phosphorus tribromide to produce 1-bromo-1-ethoxycyclopropane (which is a reactive derivative of 1-ethoxycyclopropane) and then reacting the compound with aniline to obtain an N-(1-ethoxycyclopropane) group-containing product, and a process which comprises reacting the N-(1-ethoxycyclopropane) group-containing product with sodium boron hydride and boron trifluoride-ether complex to obtain a next-stage corresponding product [J. Chem. Soc. Chem. Comm., 897, (1987)]. This process, however, includes a requisite step of producing 1-bromo-1-ethoxycyclopropane (which is thermally unstable) and therefore is inconvenient for industrial application.

Thus, industrial application of conventional processes for production of an aniline wherein a cyclopropyl group is bonded to the nitrogen atom and to production of an N-cyclopropyl-2-substituted-3,4-difluoroaniline (which is useful intermediate of the above-mentioned quinolonecarboxylic acids) has been disadvantageous and unsatisfactory in view of the yield obtained and the operability.

The present invention aims at providing processes for production, from an inexpensive raw material of high commercial availability, of N-cyclopropylanilines which are an important intermediate in producing a quinolonecarboxylic acid having a cyclopropyl group at the 1-position, a fluorine atom at the 6-position and an alkyl group, an alkoxy group or a fluorine-substituted methoxy group at the 8-position (this quinolonecarboxylic acid is a useful synthetic antibacterial agent); and intermediates therefor.

The present inventors made a study on an industrially advantageous process for producing a raw material used in production of a quinolonecarboxylic acid having a cyclopropyl group at the 1-position, a fluorine atom at the 6-position, and an alkyl group, an alkoxy group or a fluorine-substituted methoxy group at the 8-position (this quinolonecarboxylic acid has an excellent activity as a synthetic antibacterial agent), as well as on an intermediate therefor. As a result, it was found out that an N-alkoxycyclopropylaniline (which is an important intermediate for production of the above-mentioned quinolonecarboxylic acid) can be produced at a high yield by using a 3,4-difluoro-2-substituted-aniline of low cost and high industrial availability as a starting material and by reacting the starting material with a 1-alkoxy-1-trialkyl silyloxycyclopropane directly without using any conventional activation step such as bromination. It was also found out that the above-obtained N-alkoxycyclopropylaniline can be converted, by its reduction and subsequent reaction with a dialkyl alkoxymethylenemalonate, into an anilinomethylenemalonic acid; and that the anilinomethylenemalonic acid is a useful material for production of a quinolonecarboxylic acid having a cyclopropyl group at the 1-position, a fluorine atom at the 6-position and an alkyl group, an alkoxy group or a fluorine-substituted methoxy group at the 8-position; and that both the anilinomethylenemalonic acid and its intermediates are novel compounds. These findings have led to the completion of the present invention.

DISCLOSURE OF THE INVENTION

In the present invention, the above aims have been achieved by providing the inventions described in the following [1] to [5].

[1] A process for producing an N-alkoxycyclopropylaniline represented by the general formula (3):

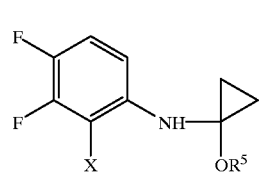

(3)

(wherein $R^5$ is an alkyl group, a cycloalkyl group, an alkenyl group, an aralkyl group or an arylalkenyl group; and X is an alkyl group, an alkoxy group or a fluorine-substituted methoxy group), which process comprises reacting, in the presence of an acid in an alcohol type solvent, a 3,4-difluoro-2-substituted-aniline represented by the general formula (1):

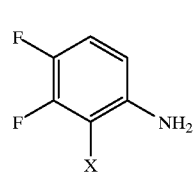

(1)

(wherein X has the same definition as given above) with a 1-alkoxy-1-trialkylsilyloxycyclopropane represented by the general formula (2):

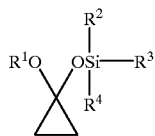

(wherein R¹ is an alkyl group, an alkenyl group, an aralkyl group or an arylalkenyl group; and R², R³ and R⁴ are each independently an alkyl group). (This process is hereinafter referred to as "the first process" as necessary.)

[2] A process for producing an N-cyclopropyl-3,4-difluoroaniline represented by the general formula (4):

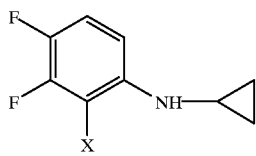

(wherein X is an alkyl group, an alkoxy group or a fluorine-substituted methoxy group), which process comprises reacting, in the presence of an acid in an alcohol type solvent, a 3,4-difluoro-2-substituted-aniline represented by the general formula (1):

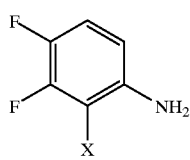

(wherein X has the same definition as given above) with a 1-alkoxy-1-trialkylsilyloxycyclopropane represented by the general formula (2):

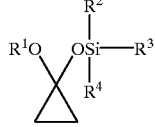

(wherein R¹ is an alkyl group, an alkenyl group, an aralkyl group or an arylalkenyl group; and R², R³ and R⁴ are each independently an alkyl group) to produce an N-alkoxycyclopropylaniline represented by the general formula (3):

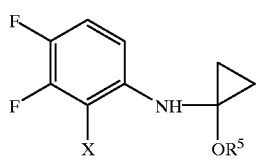

(wherein R⁵ is an alkyl group, a cycloalkyl group, an alkenyl group, an aralkyl group or an arylalkenyl group; and X has the same definition as given above) and then reducing the N-alkoxycyclopropylaniline. (This process is hereinafter referred to as "the second process" as necessary.)

[3] A process for producing an anilinomethylenemalonic acid ester represented by the general formula (5):

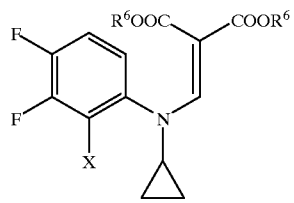

(wherein R⁶ is an alkyl group; and X is an alkyl group, an alkoxy group or a fluorine-substituted methoxy group), which process comprises reacting, in the presence of an acid in an alcohol type solvent, a 3,4-difluoro-2-substituted-aniline represented by the general formula (1):

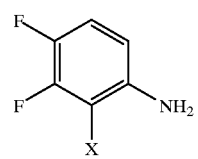

(wherein X has the same definition as given above) with a 1-alkoxy-1-trialkylsilyloxycyclopropane represented by the general formula (2):

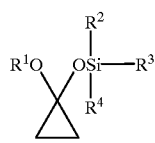

(wherein R¹ is an alkyl group, an alkenyl group, an aralkyl group or an arylalkenyl group; and R², R³ and R⁴ are each independently an alkyl group) to produce an N-alkoxycyclopropylaniline represented by the general formula (3):

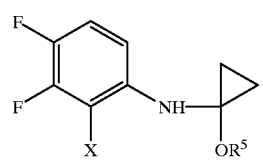

(wherein R⁵ is an alkyl group, a cycloalkyl group, an alkenyl group, an aralkyl group or an arylalkenyl group; and X has the same definition as given above), then reducing the N-alkoxycyclopropylaniline to produce an N-cyclopropyl-3,4-difluoroaniline represented by the general formula (4):

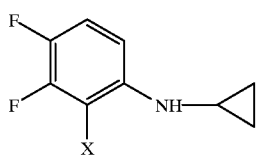

(4)

(wherein X has the same definition as given above), and reacting the N-cyclopropyl-3,4-difluoroaniline with a dialkyl alkoxymethylenemalonate. (This process is hereinafter referred to as "the third process" as necessary.)

[4] An N-alkoxycyclopropylaniline represented by the general formula (3):

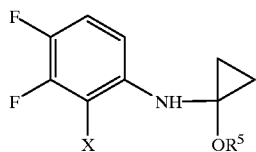

(3)

(wherein X is an alkyl group, an alkoxy group or a fluorine-substituted methoxy group; and $R^5$ is an alkyl group, a cycloalkyl group, an alkenyl group, an aralkyl group or an arylalkenyl group).

[5] An N-cyclopropyl-2-substituted-aniline represented by the general formula (6):

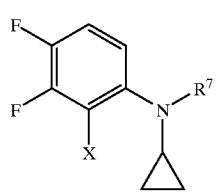

(6)

[wherein X is an alkyl group, an alkoxy group or a fluorine-substituted methoxy group; and $R^7$ is a hydrogen atom or a group:

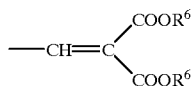

(wherein $R^6$ is an alkyl group)].

BEST MODE FOR CARRYING OUT THE INVENTION

The present invention is described in detail below.

In the first process of the present invention, an N-alkoxycyclopropylaniline represented by the general formula (3) is obtained by reacting a 3,4-difluoro-2-substituted-aniline represented by the general formula (1) with a 1-alkoxy-1-trialkylsilyloxycyclopropane in the presence of an acid in an alcohol type solvent.

The 3,4-difluoro-2-substituted-aniline used in the above reaction as a raw material can be any compound represented by the general formula (1). In the general formula (1), X is an alkyl group, an alkoxy group or a fluorine-substituted methoxy group. The alkyl group can be a straight chain or branched chain alkyl group having 1 to 6 carbon atoms (hereinafter, the carbon atoms of a substituent group or the like is abbreviated to "$C_{1-6}$" or the like, as necessary). Specific examples of the alkyl group are methyl group, ethyl group, n-propyl group, isopropyl group, n-butyl group, isobutyl group, sec-butyl group, n-pentyl group and n-hexyl group. As the compound of the general formula (1) wherein x is an alkyl group, i.e. 3,4-difluoro-2-alkylaniline, there can be mentioned, for example, 3,4-difluoro-2-methylaniline and 3,4-difluoro-2-ethylaniline.

Incidentally, the 3,4-difluoro-2-alkylaniline can be easily produced from 3,4-difluoroaniline by, for example, a process described in Tetrahedron, Vol. 48, p. 7373 (1992).

The alkoxy group represented by X of the general formula (1) can be a straight chain or branched chain alkoxy group having 1 to 6 carbon atoms. Specific examples thereof are methoxy group, ethoxy group, n-propoxy group, isopropoxy group, n-butoxy group, isobutoxy group, sec-butoxy group, n-pentyloxy group and n-hexyloxy group. As the compound of the general formula (1) wherein X is an alkoxy group, i.e. 3,4-difluoro-2-alkoxyaniline, there can be mentioned, for example, 3,4-difluoro-2-methoxyaniline and 3,4-difluoro-2-ethoxyaniline.

Incidentally, the 3,4-difluoro-2-alkoxyaniline can be easily produced from 2,3-difluoro-6-nitrophenol by, for example, a process described in JP-A-8-208617.

The fluorine-substituted methoxy group represented by X of the general formula (1) can be fluoromethoxy group, difluoromethoxy group or trifluoromethoxy group. As the compound of the general formula (1) wherein X is a fluorine-substituted methoxy group, i.e. 3,4-difluoro-2-fluorine-substituted-methoxyaniline, there can be mentioned 3,4-difluoro-2-fluoromethoxyaniline, 3,4-difluoro-2-difluoromethoxyaniline and 3,4-difluoro-2-trifluoromethoxyaniline.

The 3,4-difluoro-2-fluorine-substituted-methoxyaniline is a novel compound and can be produced by reacting 2,3-difluoro-6-nitrophenol with, for example, sodium chlorodifluoroacetate in the presence of sodium iodide and sodium carbonate in N,N-dimethylformamide to produce a 3,4-difluoro-2-fluorine-substituted-methoxy-nitrobenzene (which is also a novel compound) and then reducing the 3,4-difluoro-2-fluorine-substituted-methoxy-nitrobenzene with an iron powder or the like in the presence of sulfuric acid (see Reference Example 3 described later).

The 1-alkoxy-1-trialkylsilyloxycyclopropane represented by the general formula (2), which is another raw material in the above reaction, can be a cyclopropane having, at the 1-position, a [($C_{1-6}$)alkyl]oxy group, an alkenyloxy group which may be substituted with aryl group (e.g. phenyl group), or an aralkyloxy group [these groups correspond to $OR^1$ of formula (2)] and, also at the 1-position, a tri[($C_{1-6}$)alkyl]silyloxy group [this group corresponds to $OSiR^2R^3R^4$ of formula (2)].

Examples of the [($C_{1-6}$)alkyl]oxy group are methoxy group, ethoxy group and isopropoxy group; an example of the alkenyloxy group which may be substituted with aryl group (e.g. phenyl group) is (3-phenylallyl)oxy group; an example of the aralkyloxy group is benzyloxy group; and examples of the tri[($C_{1-6}$)alkyl]silyloxy group are trimethylsilyloxy group and dimethyl-tert-butylsilyloxy group.

As specific examples of the 1-alkoxy-1-trialkylsilyloxycyclopropane represented by the general formula (2), there can be mentioned 1-ethoxy-1-trimethylsilyloxycyclopropane, 1-methoxy-1-trimethylsilyloxycyclopropane, 1-isopropoxy-1- trimethylsilyloxycyclopropane, 1-isopropoxy-1-dimethyl-tert-butylsilyloxycyclopropane, 1-(3-phenylallyl)oxy-1-trimethylsilyloxycyclopropane, 1-(3-phenylallyl)oxy-1-dimethyl-tert-butylsilyloxycyclopropane and 1-benzyloxy-1-trimethylsilyloxycyclopropane.

The amount of the 1-alkoxy-1-trialkylsilyloxycyclopropane represented by the general formula (2) used in the above reaction is, for example, 1.0 to 1.5 moles, preferably 1.0 to 1.3 moles, per mole of the 3,4-difluoro-2-substituted-aniline represented by the general formula (1).

Incidentally, the 1-alkoxy-1-trialkylsilyloxycyclopropane can be produced by reacting ethyl β-chloropropionate of good availability with metallic sodium in the presence of chlorotrimethylsilane as described in Organic Synthesis, Vol. 63, p. 147 (1985), or by processes described in Tetrahedron Letter, Vol. 33, p. 785 (1992), Tetrahedron Letter, Vol. 24, p. 1251 (1983), Synthesis, Vol. 1, p. 58 (1982), etc.

The alcohol type solvent used in the above reaction can be an alcohol having a $C_{1-6}$ straight chain, branched chain or alicyclic structure. Specific examples thereof are methanol, ethanol, n-propanol, isopropanol, n-butanol, isobutanol, tert-butanol, n-hexanol, cyclopentanol and cyclohexanol.

The amount of the alcohol type solvent used can be, for example, 50 to 4,000 ml, preferably 200 to 3,000 ml, per mole of the 3,4-difluoro-2-substituted-aniline represented by the general formula (1).

The acid used in the above reaction can be an organic acid or an inorganic acid. The organic acid can be exemplified by aliphatic carboxylic acids including formic acid, acetic acid, propionic acid, butyric acid, etc.; aromatic carboxylic acids including benzoic acid, toluic acid, phthalic acid, etc.; aliphatic sulfonic acids including methanesulfonic acid, etc.; and aromatic sulfonic acids including benzenesulfonic acid, toluenesulfonic acid, etc.

The inorganic acid can be exemplified by hydrochloric acid, sulfuric acid and phosphoric acid. Of these acids, aliphatic carboxylic acids, particularly acetic acid and formic acid are preferred, and acetic acid is partticularly preferred.

The amount of the acid used can be, for example, 0.005 to 50 moles, preferably 0.1 to 20 moles, per mole of the 3,4-difluoro-2-substituted-aniline represented by the general formula (1).

The reaction temperature of the above reaction can be set ordinarily between room temperature and the boiling point of the solvent used, but is preferably 20 to 90° C. The reaction can be conducted merely by mixing the raw materials, the solvent and the acid at ordinary pressure and stirring them at a predetermined temperature. No pressurization is ordinarily necessary. Incidentally, the reaction time is ordinarily 0.5 to 10 hours.

In the above reaction, the alkoxy group present at the 1-position of the cyclopropyl ring of the N-alkoxycyclopropylaniline formed (said alkoxy group is derived from the 1-alkoxy-1-trialkylsilyloxycyclopropane used as a raw material) may undergo an exchange reaction with the alkoxy group of the alcohol type solvent used and, as a result, a product containing an alkoxy group derived from the alcohol type solvent may be formed. Depending upon the extent of the proceeding of the above exchange reaction of alkoxy group, the N-alkoxycyclopropylaniline of the general formula (3) may be formed in a plurality of kinds in the reaction system. The mixture thereof may be used per se in the second or third process which follows, or may be subjected to an appropriate method (e.g. rectification) for isolation of respective products.

Next, description is made on the second process and the third process.

In the second process and third process of the present invention, first, the N-alkoxycyclopropylaniline represented by the general formula (3), obtained by the above-mentioned first process of the present invention is reduced and subjected to dealkoxylation to obtain an N-cyclopropyl-3,4-difluoroaniline represented by the general formula (4) (the second process of the present invention comprises up to this step).

In this reduction reaction, as mentioned above, even if the N-alkoxycyclopropylaniline represented by the general formula (3) is formed in a plurality of kinds in the first process, the mixture of individual N-alkoxycyclopropylanilines need not be isolated from each other and can be used per se as a raw material with no problem.

As the method for the above reduction reaction, there can be mentioned, for example, a method of reacting the N-alkoxycyclopropylaniline represented by the general formula (3), with sodium boron hydride in the presence of a solvent and boron trifluoride or a metal halide.

The boron trifluoride used in the reduction reaction may be used in the form of a gas, but is preferably used in the form of a complex of boron trifluoride, such as boron trifluoride-ether complex, boron trifluoride-tetrahydrofuran complex or the like because the complex causes no problem in practical use and promises a convenient operation.

The metal halide used in the reduction reaction can be exemplified by aluminum chloride ($AlCl_3$), zinc chloride ($ZnCl_2$), iron (III) chloride ($FeCl_3$), cobalt (II) chloride ($CoCl_2$), platinum (II) chloride ($PtCl_2$), ruthenium (III) chloride ($RUCl_3$), rhodium (III) chloride ($RhCl_3$), palladium (II) chloride ($PdCl_2$), zirconium (IV) chloride ($ZrCl_4$), calcium chloride ($CaCl_2$) and lithium chloride ($LiCl$).

In the above reduction reaction, use of aluminum chloride, boron trifluoride-ether complex or boron trifluoride-tetrahydrofuran complex is particularly preferred.

The amount of the sodium boron hydride used in the reduction reaction can be, for example, 1.0 to 4.0 moles, preferably 1.0 to 2.5 moles, per mole of the N-alkoxycyclopropylaniline represented by the general formula (3); the amount of the metal halide used together can be, for example, 0.1 to 1.0 mole, preferably 0.3 to 0.7 mole (in the case of aluminum chloride), per mole of the N-alkoxycyclopropylaniline represented by the general formula (3); and the amount when boron trifluoride-ether complex or boron trifluoride-tetrahydrofuran complex is used, can be, for example, 1.0 to 5.5 moles, preferably 1.3 to 3.3 moles, per mole of the N-alkoxycyclopropylaniline represented by the general formula (3).

As the solvent used in the above reduction reaction, there can be mentioned, for example, ether type solvents such as tetrahydrofuran, diethyl ether, dimethoxyethane, diethylene glycol dimethyl ether, triethylene glycol dimethyl ether, tetraethylene glycol dimethyl ether and the like; and hydrocarbon type solvents such as benzene, toluene, xylene and the like. Any solvent can be used with no particular restriction as long as it is inactive to sodium boron hydride, metal halide and boron trifluoride-ether complex or boron trifluoride-tetrahydrofuran complex. An appropriate mixture of the above solvents may also be used. Use of an ether type solvent is preferred and, when boron trifluoride-ether complex or boron trifluoride-tetrahydrofuran complex is used, use of tetrahydrofuran is particularly preferred because stabilization of the borane formed can be expected.

The amount of the solvent used can be, for example, 50 to 3,000 ml, preferably 200 to 2,000 ml, per mole of the N-alkoxycyclopropylaniline represented by the general formula (3).

The reaction temperature of the above reduction reaction is preferably from −20° C. to the boiling point of the solvent, more preferably −5 to 80° C. Since the reaction proceeds by mere stirring at ordinary pressure, no pressure apparatus is required. Incidentally, the reaction time is ordinarily 2 to 30 hours, preferably 4 to 10 hours.

The reduction of the N-alkoxycyclopropylaniline represented by the general formula (3) can alternatively be conducted, for example, by using aluminum lithium hydride or by employing catalytic reduction.

The second process of the present invention is constituted by the first process of the present invention and the above reduction reaction step. The third process of the present invention comprises reacting the N-cyclopropyl-3,4-difluoroaniline represented by the general formula (4) obtained via the first and second processes of the present invention, with a dialkyl alkoxymethylenemalonate to form an anilinomethylenemalonic acid represented by the general formula (5).

In the dialkyl alkoxymethylenemalonate, as the alkoxy group of the alkoxy moiety bonded to the methylene carbon, there can be mentioned [($C_{1-6}$) alkyl]oxy groups, specifically, methoxy group, ethoxy group, propoxy group, isopropoxy group, butoxy group, isobutoxy group, hexyloxy group, etc. As the alkyl group of the dialkyl moiety, there can be mentioned ($C_{1-6}$) alkyl groups, specifically, methyl group, ethyl group, propyl group, isopropyl group, butyl group, sec-butyl group, tert-butyl group, etc.

The dialkyl alkoxymethylenemalonate can specifically be, for example, diethyl ethoxymethylenemalonate, dimethyl methoxymethylenemalonate, diethyl methoxymethylenemalonate, diethyl propoxymethylenemalonate, diethyl butoxymethylenemalonate, dimethyl ethoxymethylenemalonate, dipropyl methoxymethylenemalonate, dimethyl propoxymethylenemalonate or dibutyl butoxymethylenemalonate.

The above reaction proceeds by mixing 1 mole of the N-cyclopropyl-3,4-difluoroaniline represented by the general formula (4) with 1.0 to 1.5 moles, preferably 1.0 to 1.1 moles of the dialkyl alkoxymethylenemalonate and merely stirring the mixture with heating, to remove alcohol (e.g. ethanol), whereby an anilinomethylenemalonic acid represented by the general formula (5) can be produced easily.

The above reaction does not require the presence of any solvent and can be conducted ordinarily in a solvent-less state. However, a solvent inactive to the reaction may be used.

The inactive solvent usable in the reaction is, for example, an aromatic hydrocarbon, specifically, chlorobenzene, o-dichloroben- zene, toluene, xylene or the like. The amount of the inactive solvent used can be, for example, 2,000 ml or less, preferably 500 ml or less, per mole of the N-cyclopropyl-3,4-difluoroaniline represented by the general formula (4).

The reaction temperature of the above reaction is preferably 100 to 200° C., more preferably 150 to 170° C. The reaction time is ordinarily 2 to 20 hours.

The anilinomethylenemalonic acid (5) obtained by the third process of the present invention can be easily converted into an intermediate for intended quinolonecarboxylic acid by, for example, reacting the acid (5) with a dealcoholating agent such as polyphosphoric acid, polyphosphoric acid ester or the like to give rise to an intramolecular reaction for alcohol removal according to, for example, a process described in JP-A-2-45469 (see Reference Examples 1 and 2 described later).

The N-alkoxycyclopropylaniline represented by the general formula (3) obtained by the first process of the present invention, and the N-cyclopropyl-2-substituted-aniline represented by the general formula (6) obtained by the third process of the present invention are each a novel compound not appearing in any literature and are very useful as an intermediate for production of a quinolonecarboxylic acid having a cyclopropyl group at the 1-position, a fluorine atom at the 6-position and an alkyl group, an alkoxy group or a fluorine-substituted methoxy group at the 8-position (this quinolonecarboxylic acid is a useful synthetic antibacterial agent).

Next, description is made specifically on the compounds of the present invention and the processes for production thereof, by way of Examples.

EXAMPLE 1

(first process)

Into a 50-ml three-necked flask provided with a reflux condenser, a thermometer and a magnetic stirrer were fed 1.59 g (10 mmol) of 3,4-difluoro-2-methoxyaniline, 1.96 g (11.2 mmol) of 1-ethoxy-1-trimethylsilyloxycyclopropane, 8.0 g (133 mmol) of acetic acid and 20 ml of methanol. The resulting mixture was refluxed at 65° C. for 4 hours in a nitrogen current. The resulting reaction mixture was concentrated under aspirator vacuum by the use of a rotary evaporator. The resulting residue was subjected to vacuum distillation by the use of a kugel rohr to obtain 2.0 g (yield: 87.2%) of N-(1-methoxy)cyclopropyl-3,4-difluoro-2-methoxyaniline.

[Properties of N-(1-methoxy)cyclopropyl-3,4-difluoro-2-methoxyaniline]

Boiling point: 175–185° C. (outside temperature of kugel rohr)/13 mmHg

GC-MS (m/e): 229 [M$^+$]

60 MHZ $^1$H-NMR (CDCl$_3$) δ: 0.8–1.2 (4H, m, CH$_2$CH$_2$), 3.25 (3H, S, OCH$_3$), 3.92 (3H, d, J=2.0 Hz., aromatic OCH$_3$), 4.9–5.3 (1H, brs, NH), 6.5–7.4 (2H, m, aromatic nucleus hydrogen)

EXAMPLE 2

(first process)

Into a 200-ml four-necked flask provided with a reflux condenser, a thermometer and a stirrer were fed 7.96 g (0.05 mol) of 3,4-difluoro-2-methoxyaniline, 40 g (0.67 mol) of acetic acid and 100 ml of ethanol. To the resulting mixture being stirred at room temperature was dropwise added 9.24 g (0.053 mol) of 1-ethoxy-1-trimethylsilyloxycyclopropane. The resulting mixture was placed on an oil bath and refluxed at 80° C. for 3 hours with stirring, in a nitrogen current. The resulting reaction mixture was concentrated under aspirator vacuum by the use of a rotary evaporator. Lastly, the acetic acid remaining in the resulting residue was removed by the use of a vacuum pump to obtain 11.5 g of an oily substance. This oily substance was subjected to vacuum distillation to obtain 10.1 g (yield: 83.0%) of N-(1-ethoxy)cyclopropyl-3,4-difluoro-2-methoxyaniline.

[Properties of N-(1-ethoxy)cyclopropyl-3,4-difluoro-2-methoxyaniline]

Boiling point: 92–96° C./3 mmHg

GC-MS (m/e): 243 [M$^+$]

60 MHZ $^1$H-NMR (CDCl$_3$) δ: 0.8–1.1 (4H, m, CH$_2$CH$_2$), 1.11 (3H, t, J=7 Hz, CH$_3$), 3.53 (2H, q, J=7 Hz, CH$_2$), 3.92 (3H, d, J=2 Hz, OCH$_3$), 4.9–5.4 (1H, brs, NH), 6.7–6.9 (2H, m, aromatic nucleus hydrogen)

EXAMPLE 3

(first process)

Into a 200-ml four-necked flask provided with a reflux condenser, a thermometer and a stirrer were fed 7.96 g (0.05 mol) of 3,4-difluoro-2-methoxyaniline, 40 g (0.67 mol) of acetic acid and 100 ml of isopropyl alcohol. To the resulting mixture being stirred at room temperature was dropwise added 9.24 g (0.053 mol) of 1-ethoxy-1-trimethylsilyloxycyclopropane. The resulting mixture was placed on an oil bath and refluxed at 85° C. for 4 hours with stirring, in a nitrogen current. The resulting reaction mixture was concentrated under aspirator vacuum by the use of a rotary evaporator. Lastly, the acetic acid remaining in the resulting residue was removed by the use of a vacuum pump to obtain 11.3 g of a brown oily substance. This brown oily substance was subjected to vacuum distillation to obtain 7.4 g of a colorless liquid (boiling point: 93–102° C./3 mmHg). This liquid was analyzed by gas chromatography. As a result, the liquid contained 10.4% (in terms of total area %) of N-(1-ethoxy)cyclopropyl-3,4-difluoro-2-methoxyaniline and 85.7% of N-[1-(2-propyl)oxy]cyclopropyl-3,4-difluoro-2-methoxyaniline.

GC-MS (m/e):

1-ethoxy-containing product: 243 [$M^+$], 212 [$M^+$—($OCH_3$)], 184 [$M^+$—($OCH_3$)—($CH_2$=$CH_2$)]

1-(2-propyl)oxy-containing product: 257 [$M^+$], 226 [$M^+$—($OCH_3$)], 184 [$M^+$—($OCH_3$)—($CH_2$=$CHCH_3$)]

EXAMPLE 4

(first process)

Into a 200-ml four-necked flask provided with a reflux condenser, a thermometer and a stirrer were fed 7.96 g (0.05 mol) of 3,4-difluoro-2-methoxyaniline, 20 g (0.43 mol) of formic acid and 100 ml of methanol. To the resulting mixture being stirred at room temperature was dropwise added 9.24 g (0.053 mol) of 1-ethoxy-1-trimethylsilyloxycyclopropane. The resulting mixture was placed on an oil bath and refluxed at 55° C. for 4.5 hours with stirring, in a nitrogen current. The resulting reaction mixture was analyzed by gas chromatography, which indicated formation of 84.5% of N-(1-methoxy)cyclopropyl-3,4-difluoro-2-methoxyaniline.

EXAMPLE 5

(second process)

Into a 200-ml four-necked flask provided with a reflux condenser, a thermometer and a stirrer were fed 7.96 g (0.05 mol) of 3,4-difluoro-2-methoxyaniline, 12 g (0.2 mol) of acetic acid and 50 ml of methanol. To the resulting mixture being stirred at room temperature was dropwise added 10.0 g (0.0574 mol) of 1-ethoxy-1-trimethylsilyloxycyclopropane. The resulting mixture was placed on an oil bath and refluxed at 67° C. for 3 hours with stirring, in a nitrogen current. The resulting reaction mixture was concentrated under aspirator vacuum by the use of a rotary evaporator. Lastly, the acetic acid remaining in the resulting residue was removed by the use of a vacuum pump to obtain 11.52 g (crude yield: 100%) of crude N-(1-methoxy)cyclopropyl-3,4-difluoro-2-methoxyaniline (purity: 90%).

Next, 3.78 g (0.10 mol) of sodium boron hydride and 50 ml of anhydrous tetrahydrofuran were fed into a 200-ml four-necked flask provided with a reflux condenser, a thermometer and a stirrer. The resulting mixture was ice-cooled to 5° C. with stirring, in a nitrogen current. Thereto was dropwise added 14.19 g (0.10 mol) of boron trifluoride-ether complex at the same temperature, followed by stirring at 5° C. for 45 minutes. Thereto was dropwise added, at 5 to 6° C. over 40 minutes, 11.52 g of the previously-obtained N-(1-methoxy)cyclopropyl-3,4-difluoro-2-methoxyaniline. The resulting mixture was stirred at the same temperature for 1.5 hours and then at 20° C. for 5 hours. The reaction mixture was heated on an oil bath to distil tetrahydrofuran at ordinary pressure and recover 105 ml of tetrahydrofuran. The distillation residue was poured into 200 ml of water, followed by two times of extraction with 200 ml of ether. The ether layer obtained was washed with water, dried over anhydrous sodium sulfate and subjected to distillation by rotary evaporator to remove ether. The resulting residue was subjected to vacuum distillation to obtain 8.83 g (yield: 88.6%) of N-cyclopropyl-3,4-difluoro-2-methoxyaniline (purity: 96.3%).

[Properties of N-cyclopropyl-3,4-difluoro-2-methoxyaniline]

Boiling point: 78–79° C./3 mmHg

GC-MS (m/e): 199 [$M^+$], 168 [$M^+$—($OCH_3$)]

60 MHZ $^1$H-NMR ($CDCl_3$) δ: 0.5–0.8 (4H, m, $CH_2CH_2$), 2.1–2.6 (1H, m, CH), 4.3–4.7 (1H, brs, NH), 6.4–7.3 (2H, m, aromatic nucleus hydrogen)

Incidentally, even when there is used, as a raw material in the above reduction step, each of the compounds obtained in Examples 1 to 4 (after isolation as necessary), there can be obtained the same compound as the N-cyclopropyl-3,4-difluoro-2-methoxyaniline obtained in the reduction step of this Example 5.

EXAMPLE 6

(third process)

Into a 500-ml four-necked flask provided with a reflux condenser, a thermometer and a stirrer were fed 19.1 g (0.12 mol) of 3,4-difluoro-2-methoxyaniline, 96 g (1.6 mol) of acetic acid and 240 ml of methanol. To the resulting mixture being stirred at room temperature was dropwise added 25.0 g (0.14 mol) of 1-ethoxy-1-trimethylsilyloxycyclopropane. The resulting mixture was placed on an oil bath and refluxed at 67° C. for 4 hours with stirring, in a nitrogen current. The resulting reaction mixture was concentrated under aspirator vacuum by the use of a rotary evaporator. Lastly, the acetic acid remaining in the resulting residue was removed by the use of a vacuum pump to obtain 27.3 g (crude yield: 99.2%) of crude N-(1-methoxy)cyclopropyl-3,4-difluoro-2-methoxyaniline (purity: 92%).

Next, 6.81 g (0.18 mol) of sodium boron hydride and 90 ml of anhydrous tetrahydrofuran were fed into a 500-ml four-necked flask provided with a reflux condenser, a thermometer and a stirrer. The resulting mixture was ice-cooled to 5° C. with stirring, in a nitrogen current. Thereto was added 8.0 g (0.06 mol) of aluminum chloride, which brought about a temperature increase to 15° C. After the completion of the heat generation, the mixture was stirred at 5° C. for 1.5 hours, and complete dissolution of solid aluminum chloride was confirmed. Thereto was dropwise added, at 5° C., a solution of 27.3 g of the previously-obtained N-(1-methoxy)cyclopropyl-3,4-difluoro-2-methoxyaniline dissolved in 30 ml of tetrahydrofuran. The resulting mixture was stirred at the same temperature for 3 hours and further at room temperature for 4 hours. The mixture was then heated on an oil bath to distil tetrahydrofuran at ordinary pressure and recover 105 ml of tetrahydrofuran. Into a 500-ml beaker were fed 45 g of a 48% aqueous sodium hydroxide solution and 200 ml of water, and the resulting mixture was cooled on a water bath. To the mixture being stirred was dropwise added the previously obtained distillation residue. The resulting mixture was subjected to extraction with 200 ml of ether twice. The organic layer was washed with 300 ml of water twice, dried over anhydrous sodium sulfate, and subjected to solvent removal by a rotary evaporator to obtain 21.0 g (crude yield: 87.8%) of N-cyclopropyl-3,4-difluoro-2-methoxyaniline (purity: 90.8%). This product was subjected to rectification under vacuum to obtain 17.9 g (yield: 75% relative to 3,4-difluoro-2-methoxyaniline) of N-cyclopropyl-3,4-difluoro-2-methoxyaniline (purity: 98.6%, boiling point: 78–79° C./3 mmHg).

Incidentally, even when there is used, as a raw material in the above reduction step, each of the compounds obtained in Examples 1 to 4 (after isolation as necessary), there can be obtained the same compound as the N-cyclopropyl-3,4-difluoro-2-methoxyaniline obtained in the reduction step of this Example 6.

Into a 100-ml four-necked flask provided with a reflux condenser, a thermometer and a stirrer were fed 14.9 g (0.075 mol) of N-cyclopropyl-3,4-difluoro-2-methoxyaniline and 16.2 g (0.075 mol) of diethyl ethoxymethylenemalonate. The resulting mixture was stirred at 160° C. for 6 hours on an oil bath to obtain 27.3 g (yield: 98.5% relative to N-cyclopropyl-3,4-difluoro-2-methoxyaniline) of diethyl N-cyclopropyl-3,4-difluoro-2-methoxyanilinomethylenemalonate (purity: 95%).

GC-MS (m/e): 369 [M$^+$]

60 MHZ $^1$H-NMR (CDCl$_3$) δ: 0.6–0.9 (4H, m, CH$_2$CH$_2$), 1.1–1.5 (6H, m, 2CH$_3$), 3.0–3.5 (1H, m, CH), 3.7–4.4 (7H, m, OCH$_3$ and 2OCH$_2$), 6.6–7.3 (2H, m, aromatic nucleus hydrogen), 7.66 (1H, s, C═CH)

REFERENCE EXAMPLE 1

Into a 300-ml four-necked flask provided with a reflux condenser, a thermometer and a stirrer were fed 27.3 g (0.0739 mol) of diethyl N-cyclopropyl-3,4-difluoro-2-methoxyanilinomethylenemalonate and 142 g of polyphosphoric acid. The resulting mixture was stirred at 85 to 90° C. for 30 minutes on an oil bath. The reaction mixture was cooled to 40° C. and 250 ml of water was dropwise added. The resulting crystals were collected by filtration, subjected to repeated washing with water, and dried to obtain a crude 1-cyclopropyl-4-oxo-6,7-difluoro-8-methoxy-quinoline-3-carboxylic acid ester. The crude yield was 19.7 g and 82.4%. The material was recrystallized from ethanol to obtain 15.3 g (yield: 64%) of a purified product. The purified product was subjected to instrumental analysis (melting point measurement, NMR spectrometry and mass spectrometry). The analytical data obtained agreed with the data shown in the literature (see JP-B-8-9597 and JP-A-62-252772).

EXAMPLE 7

(first process)

Into a 500-ml four-necked flask provided with a reflux condenser (fitted with an anhydrous calcium chloride tube), a thermometer and a magnetic stirrer were fed 31.0 g (0.217 mol) of 3,4-difluoro-2-methylaniline, 46.9 g (0.269 mol) of 1-ethoxy-1-trimethylsilyloxycyclopropane, 53.8 g (0.896 mol) of acetic acid and 230 ml of methanol. The resulting mixture was refluxed for 4 hours with heating. The resulting reaction mixture was concentrated under aspirator vacuum by the use of a rotary evaporator. The resulting residue was concentrated using a vacuum pump to obtain 47.6 g of a solid substance. The crystals were recrystallized from n-hexane and dried to obtain 42.0 g (yield: 90.8%) of N-(1-methoxy)cyclopropyl-3,4-difluoro-2-methylaniline as white crystals.

[Properties of N-(1-methoxy)cyclopropyl-3,4-difluoro-2-methylaniline]

Melting point: 81.0–82.3° C.

GC-MS (m/e): 213 [M$^+$]

60 MHZ $^1$H-NMR (CDCl$_3$) δ: 0.7–1.3 (4H, m, CH$_2$CH$_2$), 2.05 (3H, d, J=2.22 Hz, aromatic nucleus CH$_3$), 3.26 (3H, s, OCH$_3$), 4.56 (1H, brs, NH), 6.8–7.5 (2H, m, aromatic nucleus hydrogen)

EXAMPLE 8

(first process)

Into a 200-ml four-necked flask provided with a reflux condenser (fitted with an anhydrous calcium chloride tube), a thermometer and a magnetic stirrer were fed 4.29 g (0.03 mol) of 3,4-difluoro-2-methylaniline, 6.54 g (0.0375 mol) of 1-ethoxy-1-trimethylsilyloxycyclopropane, 7.21 g (0.12 mol) of acetic acid and 60 ml of ethanol. The resulting mixture was refluxed for 5 hours with heating. The resulting reaction mixture was concentrated under aspirator vacuum by the use of a rotary evaporator. The resulting residue was concentrated using a vacuum pump to obtain 7.02 g of a solid substance. The crystals were recrystallized from n-hexane and dried to obtain 6.02 g (yield: 88.3%) of N-(1-ethoxy)cyclopropyl-3,4-difluoro-2-methylaniline as white crystals.

[Properties of N-(1-ethoxy)cyclopropyl-3,4-difluoro-2-methylaniline]

Melting point: 74.2–75.0° C.

GC-MS (m/e): 227 [M$^+$]

60 MHZ $^1$H-NMR (CDCl$_3$) δ: 0.8–1.4 (4H. m, CH$_2$CH$_2$), 1.12 (3H, t, J=7.02 Hz, CH$_3$ of OCH$_2$CH$_3$), 2.02 (3H, d, J=2.04 Hz, aromatic nucleus CH$_3$), 3.52 (2H, q, J=7.05 Hz, CH$_2$ of OCH$_2$CH$_3$), 4.50 (1H, brs, NH), 6.7–7.1 (2H, m, aromatic nucleus hydrogen)

EXAMPLE 9

(first process)

Into a 500-ml four-necked flask provided with a reflux condenser (fitted with an anhydrous calcium chloride tube), a thermometer and a magnetic stirrer were fed 28.6 g (0.2 mol) of 3,4-difluoro-2-methylaniline, 45.32 g (0.26 mol) of 1-ethoxy-1-trimethylsilyloxycyclopropane, 48.0 g (0.8 mol) of acetic acid and 400 ml of isopropyl alcohol. The resulting mixture was subjected to a reaction for 4.5 hours on an oil bath of 90° C. The resulting reaction mixture was concentrated under aspirator vacuum by the use of a rotary evaporator. The resulting concentrate was subjected to rectification to obtain 30.0 g (yield: 62.2%) of N-[1-(2-propyl)oxy]cyclopropyl-3,4-difluoro-2-methylaniline.

[Properties of N-[1-(2-propyl)oxy]cyclopropyl-3,4-difluoro-2-methylaniline]

Boiling point: 92–95° C./1.5 mmHg

GC-MS (m/e): 241 [M$^+$]

60 MHZ $^1$H-NMR (CDCl$_3$) δ: 0.7–1.4 (4H, m, CH$_2$CH$_2$), 1.08 [6H, d, J=6.30 Hz, (CH$_3$)$_2$ of CH(CH$_3$)$_2$], 2.02 (3H, d, J=2.04 Hz, aromatic nucleus CH$_3$), 3.7–4.2 [1H, m, CH of CH(CH$_3$)$_2$] 4.64 (1H, brs, NH), 6.7–7.0 (2H, m, aromatic nucleus hydrogen)

EXAMPLE 10

(first process)

Into a 50-ml flask provided with a reflux condenser (fitted with an anhydrous calcium chloride tube) and a magnetic stirrer were fed 1.43 g (0.01 mol) of 3,4-difluoro-2-methylaniline, 2.27 g (0.013 mol) of 1-ethoxy-1-trimethylsilyloxycyclopropane, 1.84 g (0.04 mol) of formic acid and 20 ml of methanol. The resulting mixture was subjected to a reaction for 4.5 hours on an oil bath of 90° C. The resulting reaction mixture was analyzed by gas chromatography, which indicated formation of 84.7% of N-(1-methoxy)cyclopropyl-3,4-difluoro-2-methylaniline.

EXAMPLE 11

(second process)

Into a 500-ml four-necked flask provided with a reflux condenser (fitted with an anhydrous calcium chloride tube), a thermometer and a magnetic stirrer were fed 28.6 g (0.2 mol) of 3,4-difluoro-2-methylaniline, 43.6 g (0.25 mol) of 1-ethoxy-1-trimethylsilyloxycyclopropane, 48.0 g (0.8 mol) of acetic acid and 200 ml of methanol. The resulting mixture was refluxed for 4 hours with heating. The resulting reaction mixture was concentrated under aspirator vacuum by the use of a rotary evaporator. The resulting residue was concentrated using a vacuum pump to obtain 42.6 g of crude N-(1-methoxy)cyclopropyl-3,4-difluoro-2-methylaniline. Next, 9.1 g (0.24 mol) of sodium boron hydride and 300 ml of anhydrous tetrahydrofuran were fed into a 1-liter four-necked flask provided with a reflux condenser, a thermometer and a stirrer. The resulting mixture was ice-cooled to 5° C. Thereto was added 16.0 g (0.12 mol) of anhydrous aluminum chloride at the same temperature, and the temperature of the reaction system increased to 15° C. When the heat generation was over, the mixture was stirred at 5° C. for 1.5 hours. Thereto was dropwise added, at 5° C. over 1 hour, a solution of 42.6 g of the previously obtained crude N-(1-methoxy)cyclopropyl- 3,4-difluoro-2-methylaniline dissolved in 100 ml of anhydrous tetrahydrofuran. The resulting mixture was stirred at 5° C. for 30 minutes, then at room temperature for 1 hour, and at 50° C. for 1 hour. The reaction mixture was partially concentrated under aspirator vacuum by the use of a rotary evaporator. The residue was dropwise added to 800 ml of water.

The resulting mixture was subjected to extraction with ethyl acetate twice. The resulting ethyl acetate layer was washed with water and dried over anhydrous sodium sulfate. The solvent in the ethyl acetate layer was removed by the use of a rotary evaporator. The residue was analyzed by gas chromatography, which indicated formation of N-cyclopropyl-3,4-difluoro-2-methylaniline (yield: 71.3% relative to 3,4-difluoro-2-methylaniline).

[Properties of N-cyclopropyl-3,4-difluoro-2-methylani- ]

Boiling point: 106–107° C./7 mmHg

GC-MS (m/e): 183 [M$^+$]

60 MHZ $^1$H-NMR (CDCl$_3$) δ: 0.3–1.1 (4H, m, CH$_2$CH$_2$), 2.00 (3H, d, J=2.04 Hz, aromatic nucleus CH$_3$), 2.2–2.6 (1H, m, CH), 3.89 (1H, brs, NH), 6.5–7.3 (2H, m, aromatic nucleus hydrogen)

Incidentally, even when there is used, as a raw material in the above reduction step, each of the compounds obtained in Examples 7 to 10 (after isolation as necessary), there can be obtained the same compound as the N-cyclopropyl-3,4-difluoro-2-methylaniline obtained in the reduction step of this Example 11.

EXAMPLE 12

(third process)

Into a 500-ml four-necked flask provided with a reflux condenser (fitted with an anhydrous calcium chloride tube), a thermometer and a magnetic stirrer were fed 28.6 g (0.2 mol) of 3,4-difluoro-2-methylaniline, 43.6 g (0.25 mol) of 1-ethoxy-1-trimethylsilyloxycyclopropane, 48.0 g (0.8 mol) of acetic acid and 200 ml of methanol. The resulting mixture was refluxed for 4 hours with heating. The resulting reaction mixture was concentrated under aspirator vacuum by the use of a rotary evaporator. The resulting residue was concentrated using a vacuum pump to obtain 43.8 g of crude N-(1-methoxy)cyclopropyl-3,4-difluoro-2-methylaniline.

Next, 9.1 g (0.24 mol) of sodium boron hydride and 300 ml of anhydrous tetrahydrofuran were fed into a 1-liter four-necked flask provided with a reflux condenser, a thermometer and a stirrer. The resulting mixture was ice-cooled to 5° C. Thereto was added 34.1 g (0.24 mol) of boron trifluoride-ether complex at the same temperature, after which the mixture was stirred at 5° C. for 1 hour. Thereto was dropwise added, at 5° C. over 1 hour, a solution of 43.8 g of the previously obtained crude N-(1-methoxy) cyclopropyl-3,4-difluoro-2-methylaniline dissolved in 100 ml of anhydrous tetrahydrofuran. The resulting mixture was stirred at 20 to 30° C. for 1 hour and at 50° C. for 3 hours. The reaction mixture was partially concentrated under aspirator vacuum by the use of a rotary evaporator. The residue was dropwise added to 800 ml of water. The resulting mixture was subjected to extraction with ethyl acetate twice. The resulting ethyl acetate layer was washed with water and dried over anhydrous sodium sulfate. The solvent in the ethyl acetate layer was removed by the use of a rotary evaporator. Lastly, the residue was subjected to vacuum distillation to obtain 31.3 g (yield: 85.5% relative to 3,4-difluoro-2-methylaniline) of N-cyclopropyl-3,4-difluoro-2-methylaniline.

Incidentally, even when there is used, as a raw material in the above reduction step, each of the compounds obtained in Examples 7 to 10 (after isolation as necessary), there can be obtained the same compound as the N-cyclopropyl-3,4-difluoro-2-methylaniline obtained in the reduction step of this Example 12.

Into a 50-ml flask provided with a reflux condenser and a magnetic stirrer were fed 2.92 g (0.0159 mol) of the previously obtained N-cyclopropyl-3,4-difluoro-2-methylaniline and 3.44 g (0.0159 mol) of diethyl ethoxymethylenemalonate. The resulting mixture was heated for 3 hours on an oil bath of 140° C. to obtain 5.53 g (yield: 98.5% relative to N-cyclopropyl-3,4-difluoro-2-methylaniline) of diethyl N-cyclopropyl-3,4-difluoro-2-methylanilinomethylenemalonate.

[Properties of diethyl N-cyclopropyl-3,4-difluoro-2-methylanilinomethylenemalonate]

GC-MS (m/e): 353 [M$^+$]

60 MHz $^1$H-NMR (CDCl$_3$) δ: 0.6–1.5 (10H, m, CH$_2$CH$_2$+ 2×(CH$_3$ of CH$_2$CH$_3$)), 2.19 (3H, d, J=1.74 Hz, aromatic nucleus CH$_3$), 2.9–3.4 (1H, m, CH), 3.6–4.5 (4H, m, 2×(CH$_2$ of OCH$_2$CH$_3$)), 6.47–7.33 (2H, m, aromatic nucleus hydrogen), 7.6 (1H, s, C=CH)

REFERENCE EXAMPLE 2

Into a 50-ml three-necked flask provided with a reflux condenser, a thermometer and a stirrer were fed 1.77 g (5 mmol) of diethyl N-cyclopropyl-3,4-difluoro-2-methylanilinomethylenemalonate and 9.5 g of polyphosphoric acid. The resulting mixture was stirred at 80° C. for 1 hour. The reaction mixture was dropwise added to 200 ml of water. The resulting crystals were collected by filtration, subjected to repeated washing with water, recrystallized from ethanol, and dried to obtain 1.17 g (yield: 76.0%) of ethyl 1-cyclopropyl-6,7-difluoro-8-methyl-4-oxoquinoline-3-carboxylate. The product was subjected to instrumental analysis (melting point measurement, NMR spectrometry, mass spectrometry). The analytical data agreed with data in the literature (JP-A-62-215572 and JP-A-63-264461).

REFERENCE EXAMPLE 3

[synthesis of 3,4-difluoro-2-fluorine-substituted-methoxyaniline]

(Production of 3,4-difluoro-2-difluoromethoxynitrobenzene)

Into a 1-liter four-necked flask provided with a reflux condenser, a thermometer and a stirrer were fed 26.3 g (0.15 mol) of 2,3-difluoro-6-nitrophenol, 29.6 g (0.2 mol) of sodium chlorodifluoroacetate, 21.2 g (0.2 mol) of anhydrous sodium carbonate, 30.0 g (0.2 mol) of sodium iodide and 200 ml of N,N-dimethylformamide. The resulting mixture was stirred at 100° C. for 1.5 hours on an oil bath and then at 120° C. for 2.5 hours. The reaction mixture was analyzed by gas chromatography. As a result, intended 3,4-difluoro-2-difluoromethoxynitrobenzene was formed at 69.6%, and 28.0% of the 2,3-difluoro-6-nitrophenol used as a raw material remained. The reaction mixture was cooled and 500 ml of water was added. The resulting mixture was subjected to extraction with 200 ml of ether. The ether layer was washed with 500 ml of water twice, dried over anhydrous sodium sulfate, and concentrated using a rotary evaporator to obtain 21.6 g of a brown oily substance. The brown oily substance was subjected to vacuum distillation to obtain 19.1 g (yield: 56.5%) of 3,4-difluoro-2-difluoromethoxynitrobenzene (purity: 97.1%, boiling point: 98–100° C./6 mmHg).

GC-MS (m/e): 225 [$M^+$], 175 [$M^+$—$CF_2$], 158 [$M^+$—$OCHF_2$]

60 MHz $^1$H-NMR ($CDCl_3$) δ: 6.73 (1H, dd, J=73 Hz, $OCHF_2$), 7.1–8.2 (3H, m, aromatic nucleus hydrogen)

(Production of 3,4-difluoro-2-difluoromethoxyaniline)

Into a 200-ml four-necked flask provided with a reflux condenser, a thermometer and a stirrer were fed 7.0 g (0.125 mol) of an iron powder, 50 ml of water and 0.1 ml of 98% sulfuric acid. The resulting mixture was heated to 95° C. on an oil bath. Thereto was dropwise added, at 95 to 100° C. over 10 minutes, 11.3 g (0.05 mol) of the previously synthesized 3,4-difluoro-2-difluoromethoxy-nitrobenzene. The resulting mixture was stirred at the same temperature for 2.5 hours. Then, a Dean-Stark trap was fitted and the mixture was refluxed with heating, whereby an oily substance was separated as a fraction of azeotropic distillation with water. The aqueous layer was subjected to extraction with 100 ml of methylene chloride. The resulting methylene chloride layer was mixed with the oily substance. The resulting mixture was concentrated, and the resulting residue was subjected to vacuum distillation to obtain 7.1 g (yield: 72.8%) of 3,4-difluoro-2-difluoromethoxy-aniline (purity: 99.1%, boiling point: 76–78° C./6 mmHg).

GC-MS (m/e): 195 [$M^+$], 155 [$M^+$—$CF_2$], 128 [$M^+$—$OCHF_2$]

60 MHz $^1$H-NMR ($CDCl_3$) δ: 3.5–4.5 (1H, brs, NH), 6.54 (1H, dd, J=74 Hz, $OCHF_2$), 6.3–7.2 (3H, m, aromatic nucleus hydrogen)

EXAMPLE 13

(first process)

Into a 50-ml three-necked flask provided with a reflux condenser, a thermometer and a stirrer were fed 2.54 g (0.013 mol) of 3,4-difluoro-2-difluoromethoxy-aniline, 2.62 g (0.015 mol) of 1-ethoxy-1-trimethylsilyloxycyclopropane, 3.90 g (0.065 mol) of acetic acid and 25 ml of methanol. The resulting mixture was refluxed with stirring, at 70° C. for 15 hours in a nitrogen current, on an oil bath. The resulting reaction mixture was concentrated under aspirator vacuum by the use of a rotary evaporator. The resulting residue was subjected to vacuum distillation to obtain 3.16 g (yield: 91.1% relative to 3,4-difluoro-2-difluoromethoxy-aniline) of N-(1-methoxy)cyclopropyl-3,4-difluoro-2-difluoromethoxy-aniline.

[Properties of N-(1-methoxy)cyclopropyl-3,4-difluoro-2-difluoro-methoxy-aniline]

Boiling point: 73–77° C./0.2 mmHg

GC-MS (m/e): 265 [$M^+$], 234 [$M^+$—$OCH_3$], 198 [$M^+$—$OCHF_2$]

60 MHZ $^1$H-NMR ($CDCl_3$) δ: 0.8–1.4 (4H, m, $CH_2$×2), 3.27 (3H, s, $OCH_3$), 5.0–5.4 (1H, brs, NH), 6.54 (1H, dd, J=74 Hz, $OCHF_2$), 6.8–7.2 (2H, m, aromatic nucleus hydrogen)

EXAMPLE 14

(third process)

Into a 50-ml three-necked flask provided with a reflux condenser, a thermometer and a magnetic stirrer were fed 3.90 g (0.02 mol) of 3,4-difluoro-2-difluoromethoxy-aniline, 4.01 g (0.0223 mol) of 1-ethoxy-1-trimethylsilyloxycyclopropane, 3.6 g (0.06 mol) of acetic acid and 20 ml of methanol. The resulting mixture was refluxed at 70° C. for 12 hours in a nitrogen current. The resulting reaction mixture was concentrated under aspirator vacuum by the use of a rotary evaporator to obtain 5.32 g of a light yellowish brown oily substance. This substance was subjected to instrumental analysis and found to contain, as a main product, N-(1-methoxy)cyclopropyl-3,4-difluoro-2-difluoro-methoxyaniline (purity: 89.4%).

Next, 1.14 g (0.03 mol) of sodium boron hydride and 20 ml of anhydrous tetrahydrofuran were fed into a 100-ml four-necked flask provided with a reflux condenser, a thermometer and a stirrer. The resulting mixture was ice-cooled to 5° C. with stirring in a nitrogen current. Thereto was dropwise added 4.33 g (0.03 mol) of boron trifluoride-tetrahydrofuran complex at the same temperature. The resulting mixture was stirred at 5° C. for 1 hour. Thereto was dropwise added, at 5 to 10° C., 5.32 g of the previously obtained N-(1-methoxy)cyclopropyl-3,4-difluoro-2-difluoromethoxy-aniline. The resulting mixture was slowly heated to 60° C. and stirred at that temperature for 12 hours to give rise to a reaction. After the completion of the reaction, the reaction mixture was cooled and added dropwise to 200 ml of water. The mixture was stirred at room temperature for 30 minutes and then subjected to extraction with 150 ml of ether. The resulting ether layer was washed with 200 ml of water, dried over anhydrous sodium sulfate, and subjected to ether removal using a rotary evaporator, to obtain 4.45 g of an oily substance. This oily substance was subjected to vacuum distillation to obtain 4.17 g (yield: 88.6% relative to 3,4-difluoro-2-difluoromethoxyaniline) of N-cyclopropyl-3,4-difluoro -2-difluoromethoxyaniline (purity: 91.3%).

[Properties of N-cyclopropyl-3,4-difluoro-2-difluoromethoxyaniline]

Boiling point: 95–100° C./6 mmHg

GC-MS (m/e): 235 [$M^+$], 168 [$M^+$—$OCHF_2$]

60 MHz $^1$H-NMR ($CDCl_3$) δ: 0.4–1.0 (4H, m, $CH_2CH_2$), 2.1–2.6 (1H, m, CH), 4.2–4.7 (1H, brs, NH), 6.4 (1H, dd, J=74 Hz, $OCHF_2$), 6.6–7.3 (2H, m, aromatic nucleus hydrogen)

Incidentally, even when there is used, as a raw material in the above reduction step, the compound obtained in Example 13, there can be obtained the same compound as the N-cyclopropyl-3,4-difluoro-2-difluoromethoxyaniline obtained in the reduction step of this Example 14.

Into a 50-ml three-necked flask provided with a reflux condenser, a thermometer and a stirrer were fed 1.18 g (0.005 mol) of the previously obtained N-cyclopropyl-3,4-difluoro-2-difluoromethoxyaniline and 2.16 g (0.01 mol) of diethyl ethoxymethylenemalonate. The resulting mixture was stirred at 170° C. for 2.5 hours in a nitrogen current and on an oil bath. The reaction mixture was transferred into a microdistillation apparatus and subjected to vacuum distillation. There were obtained, as a first fraction, 1.19 g of diethyl ethoxymethylenemalonate (boiling point: 160–165° C./0.2 mmHg) and, as a next fraction, 1.60 g (yield: 78.9% relative to N-cyclopropyl-3,4-difluoro-2-difluoromethoxyaniline) of diethyl N-cyclopropyl-3,4-difluoro-2-difluoromethoxy-anilinomethylenemalonate.

[Properties of diethyl N-cyclo-propyl-3,4-difluoro-2-difluoromethoxy-anilinomethylenemalonate]

Boiling point: 160–165° C./0.2 mmHg

GC-MS (m/e): 405 [$M^+$], 369 [$M^+—C_2H_5OH$], 332 [$M^+—COOC_2H_5$]

60 MHz $^1$H-NMR (CDCl$_3$) δ:

0.6–0.9 (4H, m, CH$_2$CH$_2$), 1.1–1.7 (6H, m, 2×(CH$_3$ of OCH$_2$CH$_3$)), 3.1–3.6 (1H, m, CH), 3.85 (2H, q, J=7.0 Hz, OCH$_2$), 4.18 (2H, q, J=7.0 Hz, OCH$_2$), 6.77 (1H, t, J=73 Hz, CHF$_2$), 6.6–7.4 (2H, m, aromatic nucleus hydrogen), 7.69 (1H, s, NC=CH—)

Industrial Applicability

The present invention provides:

industrial processes for producing at a high yield, from a 3,4-difluoro-2-substituted-aniline (a starting material) of low cost and high industrial availability, N-alkoxycyclopropyl- anilines which are raw materials for production of a quinolonecarboxylic acid having a cyclopropyl group at the 1-position, a fluorine atom at the 6-position, and an alkyl group, an alkoxy group or a fluorine-substituted methoxy group at the 8-position (this quinolonecarboxylic acid is useful as a synthetic antibacterial agent);

important intermediates (produced via the above processes) for a quinolonecarboxylic acid having a cyclopropyl group at the 1-position, a fluorine atom at the 6-position, and an alkyl group, an alkoxy group or a fluorine-substituted methoxy group at the 8-position; and processes for producing the above intermediates.

What is claimed is:

1. A process for producing an N-alkoxycyclopropylaniline represented by the general formula (3):

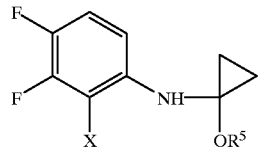
(3)

(wherein $R^5$ is an alkyl group, a cycloalkyl group, an alkenyl group, an aralkyl group or an arylalkenyl group; and X is an alkyl group, an alkoxy group or a fluorine-substituted methoxy group), which process comprises reacting, in the presence of an acid in an alcohol type solvent, a 3,4-difluoro-2-substituted-aniline represented by the general formula (1):

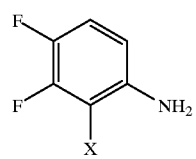
(1)

(wherein X has the same definition as given above) with a 1-alkoxy-1-trialkylsilyloxycyclopropane represented by the general formula (2):

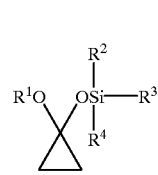
(2)

(wherein $R^1$ is an alkyl group, an alkenyl group, an aralkyl group or an arylalkenyl group; and $R^2$, $R^3$ and $R^4$ are each independently an alkyl group).

2. A process for producing an N-cyclopropyl-3,4-difluoroaniline represented by the general formula (4):

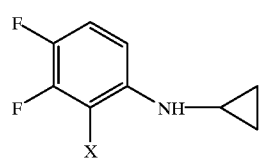
(4)

(wherein X is an alkyl group, an alkoxy group or a fluorine-substituted methoxy group), which process comprises reacting, in the presence of an acid in an alcohol type solvent, a 3,4-difluoro-2-substituted-aniline represented by the general formula (1):

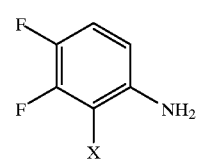
(1)

(wherein X has the same definition as given above) with a 1-alkoxy-1-trialkylsilyloxycyclopropane represented by the general formula (2):

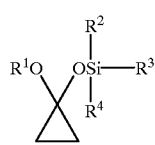
(2)

(wherein $R^1$ is an alkyl group, an alkenyl group, an aralkyl group or an arylalkenyl group; and $R^2$, $R^3$ and $R^4$ are each independently an alkyl group) to produce an N-alkoxycyclopropylaniline represented by the general formula (3):

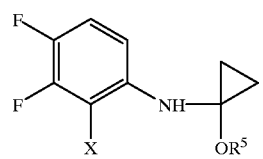
(3)

(wherein $R^5$ is an alkyl group, a cycloalkyl group, an alkenyl group, an aralkyl group or an arylalkenyl group; and X has the same definition as given above) and then reducing the N-alkoxycyclopropylaniline.

3. A process for producing an anilinomethylenemalonic acid ester represented by the general formula (5):

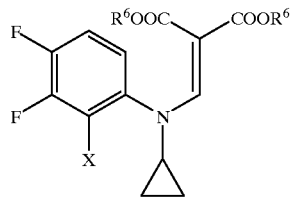
(5)

(wherein $R^6$ is an alkyl group; and X is an alkyl group, an alkoxy group or a fluorine-substituted methoxy group), which process comprises reacting, in the presence of an acid in an alcohol type solvent, a 3,4-difluoro-2-substituted-aniline represented by the general formula (1):

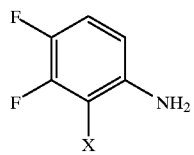
(1)

(wherein X has the same definition as given above) with a 1-alkoxy-1-trialkylsilyloxycyclopropane represented by the general formula (2):

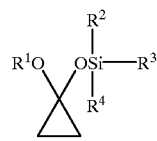
(2)

(wherein $R^1$ is an alkyl group, an alkenyl group, an aralkyl group or an arylalkenyl group; and $R^2$, $R^3$ and $R^4$ are each independently an alkyl group) to produce an N-alkoxycyclopropylaniline represented by the general formula (3):

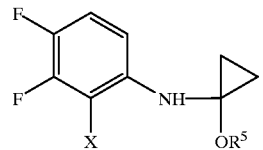
(3)

(wherein $R^5$ is an alkyl group, a cycloalkyl group, an alkenyl group, an aralkyl group or an arylalkenyl group; and X has the same definition as given above), then reducing the N-alkoxycyclopropylaniline to produce an N-cyclopropyl-3,4-difluoroaniline represented by the general formula (4):

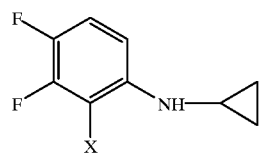
(4)

(wherein X has the same definition as given above), and reacting the N-cyclopropyl-3,4-difluoroaniline with a dialkyl alkoxymethylenemalonate.

4. An N-alkoxycyclopropylaniline represented by the general formula (3):

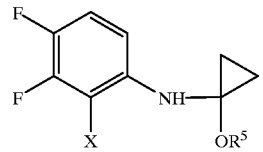
(3)

(wherein X is an alkyl group, an alkoxy group or a fluorine-substituted methoxy group; and $R^5$ is an alkyl group, a, cycloalkyl group, an alkenyl group, an aralkyl group or an arylalkenyl group).

5. An N-cyclopropyl-2-substituted-aniline represented by the general formula (6):

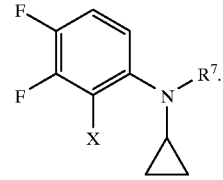
(6)

* * * * *